United States Patent [19]
Erickson et al.

[11] Patent Number: 5,622,797
[45] Date of Patent: Apr. 22, 1997

[54] DEVICE AND METHOD FOR HANDLING AND PROCESSING PHOTOGRAPHIC FILM

[75] Inventors: Wayne F. Erickson, Churchville; Stephen J. Rowan, Spencerport; William S. Raymond, Rochester, all of N.Y.

[73] Assignee: Eastman Kodak Company, Rochester, N.Y.

[21] Appl. No.: 595,706

[22] Filed: Feb. 2, 1996

[51] Int. Cl.⁶ .................................................. G03C 5/00
[52] U.S. Cl. ........................... 430/30; 430/357; 430/398
[58] Field of Search ............................. 430/30, 357, 398, 430/944

[56] References Cited

U.S. PATENT DOCUMENTS 3,661,462  5/1972  Natens ................................. 356/51
5,315,337  5/1994  Skye .................................... 354/298

Primary Examiner—Hoa V. Le
Attorney, Agent, or Firm—Arthur E. Kluegel

[57] ABSTRACT

A method for processing a silver halide photographic element having a support on the bottom and a light sensitive silver halide emulsion layer on the top, comprising:

directing a ray of infrared light in a direction so as to fall on the top side of the element;

detecting the presence or absence of infrared light reflected from the top of the element whereby the presence or absence of the element can be determined; and using the detection of the reflected infrared light to control a processing step.

The invention also provides a device capable of performing the method as described.

20 Claims, 1 Drawing Sheet

DEVICE AND METHOD FOR HANDLING AND PROCESSING PHOTOGRAPHIC FILM

FIELD OF THE INVENTION

This invention relates to a method and device useful for the handling and processing of a photographic element in which the presence of the element is ascertained by the detection of an infrared ray reflected from the side of the element opposite the support.

BACKGROUND OF THE INVENTION

A number of methods are available for the automated or semi-automated processing of photographic elements containing one or more light-sensitive silver halide emulsion layers on a support. As used herein the term "processing" is intended to include any step for handling or processing the element, whether in connection with the manufacture or development processing of the element. To simplify the terminology herein, it is assumed that the desired orientation for processing is with the support on the bottom and with the light-sensitive layer(s) on the top, and therefore reference to the top of the element means the side of the support where the sensitized layers are intended to be during processing. Of course, if the sensitized layers are intended to be other than on the top of the support during processing, top would refer to that intended side.

Automated processing in the form of so-called "minilabs" are located in supermarkets, shopping malls etc. to accomplish the automatic and accurate processing of film to provide color prints and slides. Professional offices use automated equipment to process x-rays in order to provide prompt, accurate diagnoses. In any of these systems, it is desirable to be able to automatically detect the presence of a photographic element to be processed so that the presence can be used to control a handling or processing step. For example, detecting the presence of the element in a particular location may help: determine the size of the element; detect defects in the element, perforations, etc.; count the number of elements processed; activate transport of the element to the next station for processing; turn on dryer motors to dry the element following processing; activate chemical replenishment of the processing baths; initiate splicing of the element to the preceding element for ultimate batch processing etc.

The commonly used method for detecting the presence of the photographic element is through transmissive infrared ray detection. A ray emitter is located on one side of the element and a detector on the other side. When the element is transported to a position between the emitter and detector, the ray is not transmitted because it is absorbed by the element in its path. The absorption is accomplished in part by the silver present in the element and also in part by the other film components such as absorber dyes, gel etc.

This method of detection presents problems with modern film technology. Advances in silver halide technology have resulted in the use of photographic elements which have become increasingly thinner. Moreover, the silver levels in film have been steadily reduced in order to reduce raw material costs and in order to reduce the emission of heavy metals associated with processing and disposal of silver halide materials.

As a result of modern advances, it has become a problem with certain equipment that the levels of silver and other components contained in photographic elements have been reduced to such an extent that the photographic element cannot be detected by use of the transmissive infrared detector method. Even when the element is present, it is so thin that the infrared ray is largely transmitted through the element which results in the element not being detected. While the equipment can readily handle thicker elements, it will not function properly when a thin film is processed. In some cases it may be possible to override the automatic control when a thin element is to be processed, but it is desirable to be able to rely on a completely automatic system. In other cases it may be possible to adjust the sensitivity of the infrared transmissive detector, but this may entail costly technical assistance. Further, as films become increasingly thinner, the sensitivity needed to detect the difference between the absence and presence of the element makes the system more subject to error as a result of noise or distortion.

A film splicing device available on the market uses detectors of transmitted infrared rays to ascertain the presence of film to be processed. The device also uses a single detector of reflected infrared rays located on the support or bottom side of a properly oriented photographic element to be processed as a means of determining whether the element has inadvertently been spliced with the wrong side up. This misorientation is undesirable since the rollers or other means used to transport the element should contact the support side of the element in order to avoid scratching the imaging layers during process, undesirably degrading the image. This device and method do not employ the detection of infrared rays reflected from the top or imaging layer side of the support.

It is a problem to be solved to provide a method and device for the reliable detection of both conventional and thin film during the handling and processing of a photographic element.

SUMMARY OF THE INVENTION

The invention provides a method for processing a silver halide photographic element having a support on the bottom and a light sensitive silver halide emulsion layer on the top, comprising:

directing a ray of infrared light in a direction so as to fall on the top side of the element;

detecting the presence or absence of infrared light reflected from the top of the element whereby the presence or absence of the element can be determined; and using the detection of the reflected infrared light to control a processing step.

The invention also provides a device capable of performing the method as described.

DETAILED DESCRIPTION OF THE INVENTION

Figure 1:
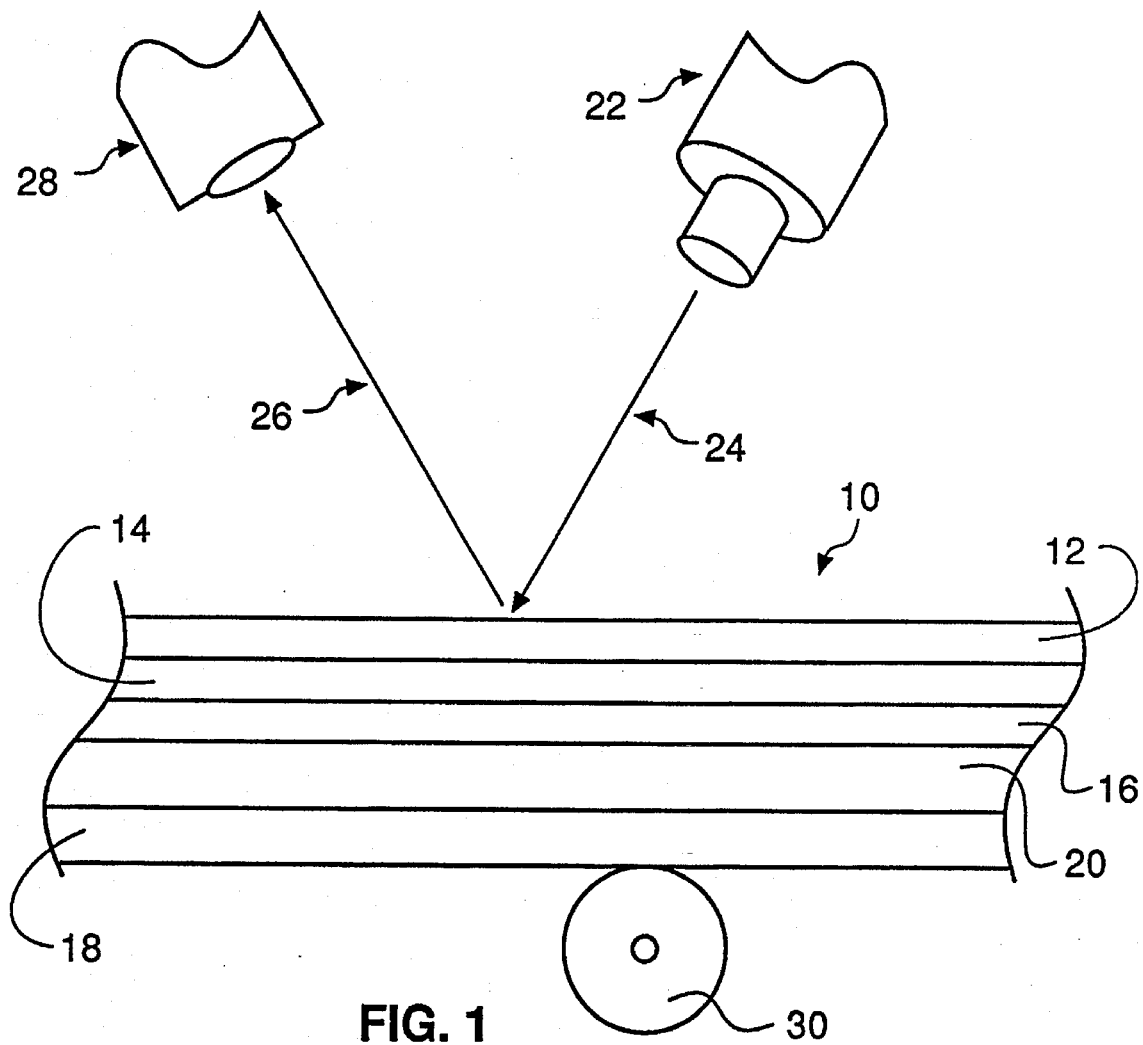
FIG. 1 is an elevation view showing a typical arrangement of a device of the invention for detecting the presence of a photographic element to be handled or processed.

As indicated in the background of the invention, as used herein the term "processing" is intended to include any step for handling or processing the element, whether in connection with the manufacture or development processing of the element. To simplify the terminology herein, it is assumed that the desired orientation for processing is with the support on the bottom and with the light-sensitive layer(s) on the top, and therefore reference to the top of the element means the side of the support where the sensitized layers are intended to be during processing. Of course, if the sensitized layers are intended to be other than on the top of the support during processing, top would refer to that intended side. As used herein, the term "tabular" grain refers to silver halide grains having a thickness of less than 0.3 micrometers (0.5 micrometers for blue sensitive emulsion) and an average tabularity (T) of greater than 25 (preferably greater than 100), where the term "tabularity" is employed in its art recognized usage as $$T=ECD/t^2$$

where
ECD is the average equivalent circular diameter of the tabular grains in micrometers and t is the average thickness in micrometers of the tabular grains.

Tabularity increases markedly with reductions in tabular grain thickness.

Concerning tabular grains in general, to maximize the advantages of high tabularity it is generally preferred that tabular grains satisfying the stated thickness criterion account for the highest conveniently attainable percentage of the total grain projected area of the emulsion, with 50% total grain projected area (%TGPA) being typical. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069, 5,061,616; 5,219,715; and 5,290,674.

Ultrathin tabular grains are tabular grains having a thickness of less than 0.07 micrometers. The ultrathin tabular grains exhibit a desired ability to effectively reflect infrared rays which enables the detection of thin films which have greatly reduced silver levels when the ultrathin grains are included in the upper layers of the film structure. The larger the content of ultrathin tabular grains in the upper layers, the more the effect can be taken advantage of. The term "upper silver halide imaging layers" or "upper layers" as used herein is intended to refer to the two imaging layers farthest from the support. In a typical color negative film this would mean the two blue sensitive layers farthest from the support. Where two blue sensitive layers are present, it would include both and where three blue sensitive layers are included it would include the two layers farthest from the support. Of course, in other layer arrangements, other image-forming layers may constitute the "upper silver halide imaging layers" farthest from the support.

More information of the manufacture and use of ultrathin tabular grains may be found in U.S. Pat. Nos. 5,219,715; 5,250,403; 5,334,469; and Research Disclosure 25330, May 1985, Kenneth Mason Publications, Ltd., Hampshire, England.

If the ultrathin proportion constitutes at least 5 wt % and more suitably at least 10, 20 or 50 wt % of the total imaging silver in the upper silver halide imaging layers, the desired benefits can be realized. Thus, if reflected infrared rays are used to determine the presence or absence of the element to be handled or processed, then both thick and thin film elements containing the indicated ultrathin proportions can be successfully processed using the same techniques. On the other hand, if the ultrathin grains are not present as specified or if the transmission rather than the reflection method of detection is used, accurate detection cannot be assured.

Accurate information as to the presence or absence of the photographic element to be processed can be used to perform operations such as splicing elements together in preparation for processing, counting the number of elements to be processed, sizing the elements, detecting defects, driving the elements during or after processing, replenishing chemicals consumed or dragged-out of the processing baths, etc.

The method of the invention is particularly suitable where the total silver laydown of the photographic element is less than 25 mg/dm$^2$; less than 20 mg/dm$^2$; and especially less than 15 mg/dm$^2$. Under these conditions of low silver laydown, many of the current infrared transmission detectors will not detect the presence of the thin element.

The infrared emitter typically provides a ray having a wavelength of 800 to 1100 nm, with the detector located and adapted to detect the reflected ray. Specific requirements for the location and orientation of the infrared ray emitter and detector are provided by manufacturers of commercially available units which may be readily adopted as required herein. The Ultima-35 film splicer manufactured by Standard Manufacturing of Chicopee, Mass. includes an emitter and detector but only on the bottom side of the element and for purposes of detecting the misorientation of the film.

An example of a device of the invention is shown in FIG. 1. Photographic element 10 is in a particular processing location and is moved continuously or intermittently via roller mechanism 30. The element is comprised of a series of successive photographic layers 12, 14, 16, 20, formed on a support 18. In this embodiment, layer 12 is a protective overcoat, layer 14 is a fast yellow layer (high blue light sensitivity), and layer 16 is a slow yellow layer (low blue light sensitivity), with layers 14 and 16 together constituting the "upper silver halide emulsion imaging layers" or "upper layers". Layer 20 represents all of the remaining layers of the element, if any, whether image-forming or otherwise, between the upper layers and the support.

Infrared ray emitter 22 emits ray 24 which is reflected as ray 26 which is then detected by detector 28. As a result of the detection or nondetection of the element, a handling or processing step is controlled in the desired manner.

EXAMPLES

Various multilayer films were tested using the method of the invention. Film 1 is a comparison film of commercial quality containing the typical high levels of silver laydown at 44.3 mg/dm$^2$. The make up of the various emulsions in the film included three dimensional grain emulsions and tabular grain emulsions. None of the emulsions in Film 1 included a significant portion of ultrathin tabular grains.

Film 2, another comparison, was prepared with a much reduced level of silver laydown. All of the layers below the upper layers for Film 2 and Film 3 were identical in makeup and included various three dimensional, tabular grain and ultrathin tabular grain emulsions. Film 3, however, contained ultrathin grain emulsions in the fast and slow yellow upper layers. As shown in Table I, the silver content of the upper levels was reduced in Film 3 compared to Film 2 but Film 3 contains a significant ultrathin tabular grain content in the upper layers.

TABLE I

Multilayer Coating - Silver Laydowns and Type

| LAYER | Silver Laydown (mg/dm² silver) | | |
|---|---|---|---|
| | Conventional High Silver Film 1 | Low Silver with Ultrathin Film 2 | Low Silver with Ultrathin in Upper Layers Film 3 |
| Overcoat | — | — | — |
| Ultraviolet Absorption | 2.2 | 1.1 | 1.1 |
| Fast Yellow | 6.5 | 6.9 | 2.5* |
| Slow Yellow | 2.9 | 3.8 | 1.7* |
| | | | 1.6 |
| Yellow Filter | 0.5 | — | — |
| Fast Magenta | 5.4 | 2.8* | 2.8* |
| Mid Magenta | 6.2 | 2.9* | 2.9* |
| Slow Magenta | 4.9 | 1.1 | 1.1 |
| Interlayer | — | — | — |
| Fast Cyan | 7.0 | 3.4* | 3.4* |
| Slow Cyan | | 4.1* | 4.1* |
| | 7.3 | 1.7 | 1.7 |
| Interlayer | No Interlayer | | |
| Antihalation | 1.5 | 1.5 | 1.5 |
| Total Imaging Silver | 40.1 | 26.7 | 21.8 |
| Total Silver | 44.3 | 29.3 | 24.4 |

*Ultrathin tabular grain emulsion. The remaining emulsions are standard thicker tabular grain and three dimensional emulsions. The low silver with ultrathin and the low silver with ultrathin in the upper layers have the same emulsions in the lower layers.

As Table II indicates, the upper layers of Film 3 contain 72.2 wt % silver as ultrathin tabular grains in the upper layers. The other two films contain no ultrathin in these two layers.

The IR reflectance is shown in measured volts at the detector. The detection must be less than 2.5 volts in order for reliable detection to occur. Thus, both the conventional high silver film and the low silver film having the requisite ultrathin tabular grains in the upper layers were detected by infrared detection. Film 2 was not detected due to the high voltage (above 2.5).

When a film like Film 3 was tested with a conventional infrared transmission detector, the presence of the film could not accurately be made. It was necessary to add additional unwanted components to the film as non imaging silver, dyes and the like in order to achieve detection by the transmission detector.

TABLE II

Results of Infrared Reflective Testing

| | Ultrathin in Upper Imaging Layers (wt % of Ultrathin of Total Imaging Silver in Upper Imaging Layers) | | |
|---|---|---|---|
| | Conventional High Silver Film 1 | Comparison Low Silver with Ultrathin in Lower Imaging Layers Film 2 | Low Silver with Ultrathin in Upper Imaging Layers Film 3 |
| TYPE | Comp | Comp | Inv |
| Ultrathin Wt % of Total Imaging Silver in Upper Imaging Layers | 0 | 0 | 72.2 |
| IR Reflectance —Volts | 0.6 | 3.6 | 2.3 |

The entire contents of the various copending applications as well as patents and other publications cited in this specification are incorporated herein by reference.

What is claimed is:

1. A method for processing a silver halide photographic element having a support on the bottom and a light sensitive silver halide emulsion layer on the top, comprising:

directing a ray of infrared light in a direction so as to fall on the top side of the element;

detecting the presence or absence of infrared light reflected from the top of the element whereby the presence or absence of the element can be determined; and using the detection of the reflected infrared light to control a processing step.

2. The method of claim 1 wherein the detection of the reflected infrared light is used to control drying of the element.

3. The method of claim 1 wherein the detection of the reflected infrared light is used to control the splicing together of two photographic elements in preparation for development processing.

4. The method of claim 1 wherein the detection of the reflected infrared light is used to control the chemical replenishment of a processing bath.

5. The method of claim 1 wherein the detection of the reflected infrared light is used to determine the size of the element.

6. The method of claim 1 wherein the detection of the reflected infrared light is used to count the number of elements which have been processed.

7. The method of claim 1 wherein the detection of the reflected infrared light is used to ascertain the presence of defects in the element.

8. The method of claim 7 wherein the detection of the reflected infrared light is used to ascertain the presence of defects in the element during manufacture of the element.

9. The method of claim 1 wherein the element is a multicolor photographic element containing at least three silver halide emulsion imaging layers sensitized to blue, green and red light, respectively.

10. The method of claim 1 wherein no detectors of infrared light transmitted through the location of the element are used to detect the presence or absence of the element.

11. The method of claim 1 wherein at least 5 wt % of the silver content of the upper silver halide imaging layers of the element is present as ultrathin tabular grains.

12. The method of claim 11 wherein at least 10 wt % of the silver content of the upper silver halide imaging layers is present as ultrathin tabular grains.

13. The method of claim 12 wherein at least 25 wt % of the silver content of the upper silver halide imaging layers is present as ultrathin tabular grains.

14. The method of claim 13 wherein at least 50% by weight of the silver content of the upper silver halide imaging layers is present as ultrathin tabular grains.

15. The method of claim 1 including directing and detecting infrared rays in at least two different locations of the element.

16. A method for the automated processing of a low silver photographic element comprising at least one silver halide imaging layer on a support, comprising:

providing an exposed element containing less than 25 mg/dm$^2$ of silver in the silver halide imaging layers wherein at least 5% by weight of the silver content of the upper silver halide imaging layers is present as ultrathin tabular grains, directing a ray of infrared light in a direction so as to fall on the imaging layer side of the support of a properly oriented photographic element to be processed;

detecting the presence or absence of the element to be processed by the corresponding detection of the presence or absence of reflected infrared light from the imaging layer side of the element, and using the detection of the reflected infrared light to control a processing step.

17. The method of claim 12 wherein the exposed element contains less than 20 mg/dm$^2$ of silver in the silver halide imaging layers.

18. The method of claim 17 wherein the exposed element contains less than 15 mg/dm$^2$ of silver in the silver halide imaging layers.

19. The method of claim 18 wherein at least 10% by weight of the silver content of the upper silver halide imaging layers is present as ultrathin tabular grains.

20. The method of claim 19 wherein at least 25% by weight of the silver content of the upper silver halide imaging layers is present as ultrathin tabular grains.

* * * * *